(12) United States Patent
Lassila et al.

(10) Patent No.: US 8,785,513 B2
(45) Date of Patent: Jul. 22, 2014

(54) FIBER-REINFORCED COMPOSITES AND METHOD FOR THE MANUFACTURE THEREOF

(75) Inventors: Lippo V. J. Lassila, Lielahti (FI); Pekka K. Vallittu, Kuusisto (FI); Sufyan Garoushi, Turku (FI); Karri Airola, Turku (FI)

(73) Assignee: Stick Tech Oy, Turku (FI)

( * ) Notice: Subject to any disclaimer, the term of this patent is extended or adjusted under 35 U.S.C. 154(b) by 413 days.

(21) Appl. No.: 12/306,673

(22) PCT Filed: Jun. 29, 2007

(86) PCT No.: PCT/FI2007/050404
§ 371 (c)(1),
(2), (4) Date: Apr. 8, 2009

(87) PCT Pub. No.: WO2008/000917
PCT Pub. Date: Jan. 3, 2008

(65) Prior Publication Data
US 2009/0258965 A1 Oct. 15, 2009

(30) Foreign Application Priority Data

Jun. 30, 2006 (FI) .................................. 20065465
Feb. 5, 2007 (FI) .................................. 20075075

(51) Int. Cl.
| | | |
|---|---|---|
| C08F 2/46 | (2006.01) |
| A61K 6/083 | (2006.01) |
| C08F 290/06 | (2006.01) |
| C08J 3/28 | (2006.01) |
| C08G 61/04 | (2006.01) |
| A61C 5/00 | (2006.01) |

(52) U.S. Cl.
USPC ............... 522/1; 523/115; 523/116; 523/117; 522/77; 522/81; 522/121; 522/129; 522/142; 522/146; 520/1; 433/228.1

(58) Field of Classification Search
USPC ............. 523/115–117; 522/77, 81, 121, 129, 522/142, 146, 1; 433/228.1; 520/1
See application file for complete search history.

(56) References Cited

U.S. PATENT DOCUMENTS

| | | | |
|---|---|---|---|
| 4,894,012 A * | 1/1990 | Goldberg et al. ............. 433/215 |
| 5,328,372 A * | 7/1994 | Reynaud et al. .............. 433/220 |
| 6,186,791 B1 | 2/2001 | Karmaker et al. |
| 6,197,410 B1 | 3/2001 | Vallittu et al. |
| 6,270,348 B1 | 8/2001 | Petersen |
| 6,334,775 B2 * | 1/2002 | Xu et al. .................... 433/228.1 |
| 6,403,676 B1 | 6/2002 | Jia et al. |
| 6,433,037 B1 | 8/2002 | Guzauskas |
| 6,846,181 B2 * | 1/2005 | Karmaker et al. ......... 433/212.1 |
| 6,872,076 B2 * | 3/2005 | Karmaker et al. ......... 433/201.1 |
| 7,001,181 B2 | 2/2006 | Kangasniemi et al. |
| 7,183,334 B2 * | 2/2007 | Guzauskas ...................... 522/31 |
| 2001/0026913 A1 | 10/2001 | Xu et al. |
| 2002/0082316 A1 | 6/2002 | Karmaker et al. |
| 2002/0086266 A1 | 7/2002 | Karmaker et al. |
| 2003/0203333 A1 | 10/2003 | Vallittu et al. |
| 2004/0038182 A1 | 2/2004 | Zappini et al. |
| 2004/0241614 A1 | 12/2004 | Goldberg et al. |

FOREIGN PATENT DOCUMENTS

| | | |
|---|---|---|
| WO | WO-96/25911 A1 | 8/1996 |
| WO | WO-99/45890 A1 | 9/1999 |
| WO | WO-03/105785 A1 | 12/2003 |

OTHER PUBLICATIONS

Vakiparta et al., "Flexural Properties of Glass Fiber Reinforced Composite with Multiphase Biopolymer Matrix", Journal of Materials Science: Materials in Medicine 15, 2004, pp. 7-11.

* cited by examiner

*Primary Examiner* — Ling Choi
*Assistant Examiner* — Jessica E Whiteley
(74) *Attorney, Agent, or Firm* — Birch, Stewart, Kolasch & Birch, LLP

(57) ABSTRACT

The present invention relates to fiber-reinforced composites, particularly application-oriented composites useful in dental and medical applications/appliances, such as fiber reinforced dental composites, and to a method for the manufacture thereof. Particularly the invention concerns random glass fiber-reinforced restorative composite resins with semi-interpenetrating polymer network matrix and their use in dental applications like cavity fillings, core composites, provisional and semi-permanent crown and bridge composite, cements and adhesives.

9 Claims, 6 Drawing Sheets

FIBER-REINFORCED COMPOSITES AND METHOD FOR THE MANUFACTURE THEREOF

FIELD OF INVENTION

The present invention relates to a method for the manufacture of fiber-reinforced composites (FC), using a combination of highly viscous glass fiber bundles, particulate filler and curable resin, yielding a FC product, which when cured has unique application-oriented properties. Further, the invention relates to fiber-reinforced composites (FC) and application-oriented composites useful in dental and medical applications/appliances, obtainable by said process. The invention relates further to the application-orientation property of the FC. The invention also concerns fiber-reinforced restorative composite resins with semi-interpenetrating polymer network matrix and their use in dental applications/appliances like cavity fillings, core composites, provisional and semi-permanent crown and bridge composite, cements and adhesives.

STATE OF THE ART

Dental restorative filling composite resins were introduced to the dental community already in 60's, and still, after many significant material improvements, restorative composites suffer from lack of mechanical properties and problems relating to polymerization shrinkage. Clinical studies have shown that direct fillings' composites fail predominantly because of the following three reasons: Occlusal wear, secondary caries and fracture of restorative filling composite. Due these problems, it is still controversial whether restorative composites should be used in large high-stress bearing applications such as in direct posterior restorations. The relatively high brittleness and low fracture toughness of current composites make their use in large stress-bearing restorations generally less preferable.

U.S. Pat. No. 6,403,676 teaches reinforcing of dental composites with ground, densified and embrittled S-glass fiber particles, obtained by grinding S-glass fiber particles, which have been densified and embrittled by heating at a temperature below the softening point of the glass fibers. The glass fiber particles have average particle size of less than about 80 µm. The composite comprises also a polymeric matrix precursor and optionally conventional fillers, and it is useful as direct filling material having the feel and workability of widely used amalgam.

Composites comprising chopped fiber-reinforcement are disclosed in U.S. Pat. No. 6,270,348, containing individual fibers having fiber length of about 1-3 mm added to the composites. Suitably silane-treated quartz fibers, ceramic and polyethylene fibers, optionally with radio-opaque material, were added to dental composites. Composites containing 10-22 weight % of quartz fibers exhibited flexural strength over 200 MPa.

Continuous fibers, resin-fiber pastes and fiber-reinforced preforms for inserting into tooth cavities to form high-strength dental restorations are described in U.S. Pat. No. 6,334,775. Accordingly, continuous fibers are placed on the bottom of a dental cavity to reach at least 60% of the maximum width of the cavity, and the rest of the cavity is filled with a conventional dental composite. 5-100% of the fibers are continuous fibers, distinct from short fibers.

A polymer pre-impregnated fiber material consisting of continuous fibers, also known as prepreg, is presented in U.S. Pat. No. 6,197,410. The prepreg is particularly useful in restorative dentistry. Also a polymethyl methacrylate (PMMA) based semi-interpenetrating polymer network (semi-IPN) matrix is disclosed, which is suitable as polymer matrix in denture base materials.

Glass fibers have been suggested for reinforcement in dental polymers for over 30 years. They have good reinforcing efficiency and esthetic qualities comparable to those of carbon or aramid fibers. The reinforcing efficiency of fibers depends on many variables, including resins used, quantity of fibers in the resin matrix, length of fibers, form of fibers, orientation of fibers and reinforcing factor (Krenchel factor), adhesion of fibers to the polymer matrix, and impregnation of fibers with the resin.

Short random fibers provide an isotropic reinforcement effect in multi-directions instead of one or two directions, and thus very limited strengthening effect.

Typically commercial dental restorative materials (known as ready-to-use compositions) with reinforcing fibers have fiber length of 80-200 µm. One of the major drawbacks of these known short fiber composites is the very limited strengthening effect of short fibers. Even though providing some benefits to the composites, the performance of cut fiber composites resembles the performance of typical particle filler loaded dental composites having inferior flexural strength and tensile strength. The compromised length of fibers inevitably sets limits to the performance, as can also be seen in the comparative example illustrated in FIG. 1.

A common problem of the fiber-reinforced composites according to the state of the art is that they have rough surface comprising non-spherical and relatively large particles and fibers sticking out from the surface. Large particle means here that one dimension of the particle exceeds 10 µm. This results in poor polishability of ready polymerized fillings and problems with finishing, whereby the surface of the filling remains rough and therefore prone to bacterial colonization and for colorization. For eluding the problems relating to finishing of dental fillings U.S. Pat. No. 6,197,410 and U.S. Pat. No. 6,334,775 suggest a further operation for covering of the reinforcing composites by any conventional dental filling material with proper finishing properties.

There also appear certain difficulties relating to the known manufacturing methods of fiber reinforced dental composites. When composites containing long fibers having a length of 1 mm or more are produced at laboratory conditions using small-scale gentle preparation by hand, desired products are obtained. However, up-scaled manufacture of dental composites is too violent to single fibers. The long fibers are easily broken or cut in the processing to very short fibers, which are not able to provide the desired reinforcing effect. Furthermore, the fibers tend to agglomerate during the processing resulting in poorly wetted clusters of particles.

Embrittlement of fibers during processing is also described as an alternative manufacturing method in U.S. Pat. No. 6,403,676.

At present no dental restorative composites with semi-IPN-polymer matrix, in combination with glass fibers, have been disclosed. Based on the above it can be seen that there exists a need for improved fiber reinforced composites and for a method for the manufacture thereof.

OBJECT OF THE INVENTION

An object of the invention is a method for the manufacture of fiber-reinforced composites, particularly random fiber-reinforced composites.

A further object of the invention is a method for the manufacture of fiber-reinforced composites, particularly application-oriented composites.

A further object of the invention is to provide improved fiber-reinforced composites, particularly random fiber-reinforced composites.

A further object of the invention is to provide improved fiber-reinforced composites, particularly application-oriented composites.

A still further object of the invention is the use of said fiber-reinforced composites in dental applications/appliances like restorative fillings, core composites, provisional and semi-permanent, and permanent crown and bridge composites, cements, adhesives and CAD/CAM blocks.

A further object of the invention is the use of said fiber-reinforced composites in biomedical applications, such as in orthopedics bone cements, bone support devices, and in head and neck surgery as artificial bone materials.

A still further object of the invention is the use of the fiber-reinforced composites in forming the core structure of implantable bio-stabile orthopedic devices, such as fixation plates, screws, nails and joints for hip, knee and shoulder.

A still further object of the invention is glass fiber filled and particularly E-glass glass fiber filled dental composites with semi-IPN-polymer matrix.

SUMMARY OF THE INVENTION

The present invention provides a method for the manufacture of fiber-reinforced composites and particularly application-oriented composites. The present invention also provides fiber-reinforced composites and particularly application-oriented composites, and their use in dental and medical applications/appliances. Application-orientation takes place when the fiber-reinforced composites, particularly the fibrous glass reinforced composites are applied into a tooth cavity or, according to another embodiment of invention, into a mould or perform, for the manufacture of for example an orthopedic device.

Application-oriented composite means here that random, 3-dimensionally oriented fibers of the composite are preferably oriented 2-dimensionally or even 1-dimensionally during the application of the composite as layers at the desired location.

Reinforcing factor means here Krenchel's reinforcing factor as defined in Vishu, S: Handbook of plastic testing technology, 2 ed. New York: John Wiley; 1998. pp. 546, according to which 3D random orientation has a coefficient of 0.2, whereas 2D random orientation has a coefficient of 0.38. This behaviour and Krenchel's factor can be applied also beyond the reinforcing effect, eg. in thermal expansion and hydroscopic swelling of the composite caused by water and polymerization shrinkage.

Random fiber-reinforced composite or fibrous composite means here that the reinforcing factor of fibres in the composite structure is more than 0.25 as in the parallel oriented fibres in 45 degrees against the tension force and less than 1.0 as with the along the axis of tension force. A preferred range of the reinforcing factor is from 0.25 to 0.5.

Curing refers here to polymerization and/or cross-linking.

Prepreg means here a semi-manufactured product, which is non or partly polymerized, yet still deformable.

Matrix means here continuous phase of the composition, and by non-cured matrix is meant that the matrix is deformable but can be cured to a hardened state.

DETAILED DESCRIPTION OF THE INVENTION

Figure 1:
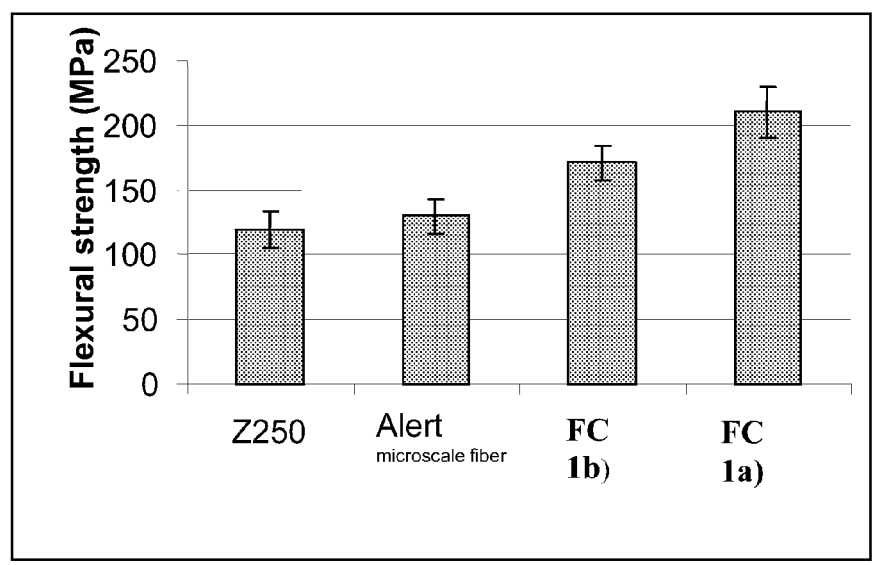
FIG. 1 presents a comparison of mechanical properties (flexural strength).

Surprisingly it was found, that the problems relating to the fiber-reinforced composites according to the state of the art and to their manufacturing processes can be avoided or at least substantially decreased by the composite and method according to the invention, wherein the desired, fiber-reinforced composites suitable for dental and medical applications/appliances are obtained. The invention is now described more in detail in the following.

The fiber-reinforced composite according to the invention comprises a curable or partially curable monomer system, a filler system and conventional polymerization initiators and/or accelerators. The filler system comprises at least one prepreg containing highly viscous fiber bundles, the fiber length being of 0.5-100 mm, preferably 3-20 mm, and optionally at least one particulate filler selected from conventional particulate fillers having a particle size from 0.1 to 100 µm and nanoscale particulate fillers having a particle size less than 0.1 µm. The prepreg is in the form of pieces having a length of 0.5-100 mm, preferably 3-20 mm, and the prepreg pieces comprise fibers having fiber length of 0.5-100, preferably 3-20 mm.

The composite comprises 5-70 wt %, preferably 10-60 wt % and particularly preferably 15-30 wt % of the monomer system comprising at least one curable monomer, and 30-95 wt %, preferably 40-90 wt % and particularly preferably 70-85 wt % of the filler system. The filler system may optionally comprise 0-90 wt %, preferably 0-80 wt % of at least one particulate filler selected from conventional particulate fillers and nanoscale particulate fillers. However, it should be noted, that the percentage of the weight content of the particulate filler may have large variations according to density of used particulate filler. For example radio-opacity fillers, such BaAlSiO$_2$, BaSO4 and ZrO$_2$ have much higher densities than conventional fillers like SiO$_2$.

Filler System

The filler system comprises at least one prepreg consisting of a polymer matrix and fiber bundles, the fiber length in the prepreg being of 0.5-100 mm, preferably 3-20 mm, and optionally 0-90 wt % of at least one particulate filler selected from conventional particulate fillers having a particle size from 0.1 to 100 µm and nanoscale particulate fillers having a particle size less than 0.1 µm. The prepreg in the composite is in the form of pieces having a length of 0.5-100 mm, preferably 3-20 mm and the prepreg is chopped or cut into pieces before the manufacture of the composite. The prepreg and the method for the manufacture of it are disclosed in U.S. Pat. No. 6,197,410, incorporated here by reference.

The prepreg comprises fiber bundles comprising 50-95 wt %, preferably 60-90 wt % and particularly preferably 65-75 wt % of fibers in 5-50 wt %, preferably 10-40 wt % and particularly preferably 35-45 wt % of a polymeric matrix. The fiber bundles comprise at least two, preferably 3-10000 fibers and particularly preferably the amount of fibers is 1000-2000 fibers per bundle.

The fiber has a diameter of 0.05-100 μm, preferably 1-25 μm and particularly preferably 5-15 μm.

Suitable fibers in the prepreg are either inorganic or organic fibres. As examples of suitable fibres can be mentioned fibres of bioactive glass, glass fibers, quartz fibers, alumina fibers, zirconia fibers, metallic and other ceramic fibers, carbon/graphite fibers and polymeric fibers, such as UHMWPE fibers, aramide fibers, self-reinforced polymer fibers, fibers based on polyphenoles, degradable and biodegradable fibres, and sol-gel derived silica fibres and any mixtures thereof. Preferably silanized glass fibers like E-glass fibers (electrical grade) are used. The glass fibers may be surface treated by any method known in the art using conventional compounds for silanization, such as methoxypropyl trimethoxy silane. Suitably the fibers can also be used as combinations, such as combinations of stabile glass fibers with degradable bioactive fibers.

The polymer matrix of the prepreg consists a first matrix component, a second matrix component and a third matrix component consisting of high molecular weight organic molecules, e.g. of thermoplastics. The third matrix component is preferably distributed between the fibres. The first matrix component and the third matrix component form a gel. The prepreg preferably contains ingredients necessary to initiate the polymerization at a desired point of time. All the necessary ingredients can be included in the prepreg, except for the case where the curing process is based on auto-polymerization. In this case, the initiator and activator system should be inserted into separate composites, which are mixed together just before use.

The prepreg may also contain additives such as bioactive or inert filler materials, colour pigments or therapeutic materials. Although the membrane covering the fibers can be made just by polymerization of the monomer on the surface layer of the prepreg, it is preferable to create the membrane by dipping the preform in a separate solution of a polymer.

A suitable process for the preparation of the prepreg comprises the following steps:
a) impregnating the fibres with a liquid containing high molecular weight organic molecules, such as PMMA (polymethyl methacrylate) molecules with molecular weight from 190,000 to 900,000 or epsilon-caprolactone/PLA, epsilon-caprolactone, D-polylactide- and L-polylactide-, PLA- or PGA-molecules or other thermoplastic biocompatible polymer molecules having a molecular weight in the range from 5,000 to 400,000 in a rapidly evaporating organic solvent, such as tetrahydrofuran (THF), acetone, or the like; said liquid optionally containing additives such as different inert or bioactive fillers containing elements, such as Si, Ca, P, Ba, Mg, K, Ti, F, oxides or other compounds of said elements, colour pigments, inert ceramics, hydroxy apatite (HA) or other Ca-phosphates, $Al_2O_3$, $ZrO_2$, xerogels, bioactive glasses or functionally bioactive or therapeutically active molecules, antigenes, antibiotics, disinfectants, radio opaque materials, organic acids such as maleic acids, polyacrylic acid, or the like;
b) evaporating the solvent, which results in a highly porous polymer mass between the fibres,
c) wetting the preform obtained in step b) in a monomer system, such as BISGMA-TEGDMA system, or in a multifunctional cross-linker (hyperbranched molecules like dendrimers, multifunctional macromers etc), said system optionally containing necessary chemical compounds required for subsequent polymerization of the monomers or dendrimers, where said monomers or dendrimers at least partly dissolve the highly porous thermoplastic mass between the fibres,
d) pultruding the preform obtained in step c) through a mixture of a solvent and high molecular weight organic molecules in order to create a well bound IPN polymeric membrane for coverage of the fibres of the prepreg,
e) optionally covering the membrane with small particles of polymer, inert or bioactive fillers containing elements such as Si, Ca, P, Ba, Mg, K, Ti, F, oxides or other compounds of said elements, colour pigments, inert ceramics, hydroxy apatite (HA) or other Ca-phosphates, AltO3, ZrO2, xerogels, bioactive glasses or functionally bioactive or therapeutically active molecules, antigenes, antibiotics, disinfectants, radio opaque materials, and
f) optionally packing the prepreg in a package containing metal foil bottom and optionally two layers of polymer sheet coverage; the closest to the prepreg being clear translucent sheet and the outermost sheet being a translucent sheet capable of avoiding initiation of light-polymerization by visible light in the case of light-polymerizable prepreg.

The prepreg, which is suitably in the form of unidirectional fibres, contains a polymer-monomer gel, which binds the fibres sufficiently strongly together, and a thin polymeric high molecular weight thermoplastic membrane, which covers and protects the fibres of the prepreg. The slightly sticky thermoplastic membrane allows the prepregs to have inter-strand adhesion before polymerization.

The monomers used in the first matrix component of the prepreg can be any kind of monomer or combination of monomers. Suitable monomers are selected from the group consisting of non-degradable bisphenol A-glycidyl dimethacrylate (BISGMA), triethylenglycol dimethacrylate (TEGDMA), hydroxyethyl dimethacrylate (HEMA), urethanedimethacrylate (UDMA), bisphenol A polyethylene glycol diether (BISEMA), 1,6-hexanediol dimethacrylate HDDMA, EGDMA, monomethacrylates, dimethacrylates or oligomeric acrylates. Optionally the monomer system can be based on ring-opening eg. epoxy-based chemistry. Degradable and biodegradable resin systems can also be used.

Among preferable monomers can be mentioned 2,2-bis[4-(2-hydroxy-3-methacroyloxy)phenyl]propane (BISGMA), triethyleneglycol dimethacrylate (TEGDMA), methylmetacrylate (MMA), dimethacylate of 1,3- or 1,4-butanediol (BDDMA), urethane dimethacrylate (UDMA) and hydroxyethyldimethacrylate (HEMA).

The polymer used in the second matrix component of the prepreg is preferably a thermoplastic polymer in its dissolved form, such as PMMA. Thermoplastic polymers are preferred because they can dissolve into resins applied around the prepreg. Suitable polymers are homo- or co-polymers of acrylates or methacrylates, preferably polymethyl methacrylate, polyethyl methacrylate, co-polymers of methyl and ethyl methacrylates, poly(2-ethoxyethyl)methacrylates. Also polyphenoles, polycaprolactame, D-polylactide, L-polylactide, PLA- and PGA-molecules, polyorthoesters, bioactive and biocompatible polymers are suitable to be used as thermoplastic polymers.

The polymer used in the third matrix component of the prepreg can be any thermoplastic polymer in dissolved form. Suitable polymers are high molecular weight polymers, such as homo- or co-polymers of acrylates and methacrylates, preferably polymethyl methacrylate (PMMA) most often used in dentistry and orthopedic surgery, polyethyl methacrylate, co-polymers of methyl and ethyl methacrylates, poly(2-ethoxyethyl)methacrylates, hyberbranched polymers or dendrimers selected from the group consisting of acrylate or methacrylate functionalised multifunctional and hyperbranched cross-linkers, such as epoxides, polyurethanes, unsaturated polyesters and polyethers, oligomers. Suitable polymers are also epsilon-caprolactone (PLA), epsilon-caprolactone, D-polylactide- and L-polylactide-, PLA-, PGA-molecules, polyorthoesters, polyphenolenes, polycaprolactame and other bioactive or biocompatible polymers.

During the fabrication process of the pregreg, the polymer chains of the preimpregnation polymer (third matrix component) (e.g. PMMA) are dissolved by the monomers (e.g. BISGMA-TEGDMA) or dendrimers of the first matrix component and they form a highly viscous gel containing high-molecular-weight molecules (PMMA) in monomeric phase (BISGMA-TEGDMA). The gel and the thin high-molecular-weight membrane (second matrix component) bind the fibres together and eliminate fraying of the fibres during handling. Either the monomeric phase or the high-molecular-weight molecule phase, or both, can contain chemical compounds required to initiate the polymerization reaction. The high molecular weight component of the third matrix component is distributed between the fibers.

The particulate filler is selected from conventional particulate fillers having a particle size from 0.1 to 100 μm and nanoscale particulate fillers having a particle size not more than 0.1 μm.

Conventional particulate fillers are selected from color pigments, inert ceramics, xerogels, inorganic salts, such as phosphates and oxides of Si, Ba, AL, Ca, P, Ba, Zr, Al, Mg, K, Na, Ti and F, preferably fumed silica, colloidal silica, amorphous silica, quartz, alumina silicate, barium silicate glass, fluorosilicate glass, zirconia, calcium oxides, hydroxyapatites, titania, calcium phosphate, bioactive or bio-soluble glasses and combinations thereof.

The nanoscale particulate fillers are selected from inorganic fillers such as silica, organic polymer fillers and organic-inorganic silsesquioxane based fillers.

The viscosity of the polymer matrix of the highly viscous prepreg is at least 200 Pa s, preferably at least 500 Pa s and particularly preferably 1000 Pa s.

Monomer System

The monomer system of the composite according to the invention comprises at least one curable monomer, preferably a light or chemically curable monomer selected from hydroxyethyl methacrylate, multifunctional dimethacrylates, multifunctional acrylates, multifunctional methacylates, multifunctional epoxides, preferably bisphenol A-glycidyl dimethacrylate (BISGMA), bisphenol A polyethyleneglycol diether (BISEMA), triethyleneglycol dimethacrylate (TEGDMA), tetraethyleneglycol dimethacrylate (TeEGDMA), neopentylglycol dimethacrylate (NPGDMA), dimethacrylates of polyethyleneglycols, urethane dimethacrylate (UDMA), 1,3- and 1,4-butanediol dimethacrylate (BDDMA), 1,6-hexanediol dimethacrylate (HDDMA), 2-hydroxyethanol methacrylate (HEMA) and light curable biodegradable resins.

The composite contains additional ingredients necessary to initiate polymerization, such as polymerization initiators and/or sensibilizers in an amount of 0.1-3 wt-%, accelerators and stabilizers. The polymerization initiator may be a photo-initiator such as benzoin methylether, benzyl ketal, camphor quinone or acylphinoxide, or a redox initiator such as dibenzoyl peroxide/aromatic or aliphatic tertiary amine, tertiary butyl peroxybenzoate/ascorbic acid/metal compound, or other suitable polymerization initiator/accelerator/sensibilizer or a mixture thereof.

The composite according to the invention comprises a multiphase polymer matrix comprising typically a first matrix component consisting of at least one monomer, oligomer, hyberbranched polymer or dendrimer, and a second matrix component consisting of at least one high molecular weight compound, such as PMMA, and an optional third matrix component, forming together a semi-interpenetrating polymer network (IPN).

The composite according to the invention is manufactured by compounding to 5-70 wt %, preferably 10-60 wt % and particularly preferably 15-30 wt % of the monomer system comprising at least one curable monomer, 30-95 wt %, preferably 40-90 wt % and particularly preferably 70-85 wt % of the filler system comprising the prepreg, chopped or cut into pieces, and 0-90 wt %, preferably 0-80 wt % of at least one particulate filler selected from conventional particulate fillers and nanoscale particulate fillers, and polymerization initiators and/or accelerators using suitable equipment known in the art. Before compounding the prepreg containing fiber bundles is chopped or cut with any cutter or chopper available according to the state of the art to pieces with a length of 0.5-100 mm, preferably 3-20 mm, depending on the desired use and thickness of the applied layer.

A fiber-reinforced restorative composite resins with semi-interpenetrating polymer network matrix is obtained. The polymer matrix of the prepreg is also a semi-IPN polymer matrix, but it is essentially stickier and having higher viscosity than polymeric matrix of the composite according to the invention, formed from the monomer system.

The fiber-reinforced composite according to the invention is a stabile product and it may be applied to desired form and cured. The fiber-reinforced composites, particularly the random fiber-reinforced composites are application oriented, when the composite is applied into tooth cavity or into a mould or preform, when for example manufacturing an orthopedic device.

The long, random, 3-dimensionally oriented fibers or fibre bundles of the composite are typically oriented 2- or even 1-dimensionally during the application of the composite by an application instrument, such as a compressing or levelling instrument, suitable a hand instrument like a spatula or other dentist's hand instrument; brush, applicator, syringe, application tip, mould; or other compressing or transferring aid like releasing paper or film etc. If the composition is applied on a plane, layer by layer, the orientation obtained is typically 2-dimensional.

The overall application orientation may also be 3-dimensional but still application oriented when compared to a conventional 3D bulk random oriented composite if the coated, levelled or covered surface or plane is contoured and the application is carried out with contouring instruments similar to the application instruments listed above.

1-dimensional application orientation is achieved if the composite is applied, dispersed or spread out from the syringe with a tip and the tip is moved along the longitudinal axis of orienting fibres during the application. Applying the composite along the longitudinal axis a "nearly" 1-dimensional wire or filament is achieved, where the 1-dimensional filament comprises single and parallel fibres or bundles of fibres and if this 1-dimensional filament is slightly spread in other dimension, a two dimensional thread, band or ribbon is achieved.

The polymerization and curing of the composite may be carried out with light, chemically, by heat, with ultrasonic radiation, gamma-radiation, electron-beam radiation or other electromagnetic radiation or by any combinations of them.

The composite according the invention has several advantages. The pre-impregnation of fiber bundles in the manufacture of the prepreg enables the manufacture of the random fiber reinforced composites with minor grinding and breaking the fibers and optimum wetting of fibers. In the resulting applied and cured random fiber composite, the fibers are distributed evenly to produce the desired fiber structure.

This random fiber-reinforced composite is particularly useful in dental applications/appliances such as restorative and prosthodontic materials, as restorative fillings, core composites, adhesives, liner materials, sealing materials, cementing materials and luting material, in cavity filling materials, root canal post-cementing materials, provisional, semi-permanent and permanent crown and bridge composites, adhesives and CAD/CAM block. And further, the random fiber reinforced composite can be used in other biomedical application eg. in orthopedics bone cement or bone support devices and in maxillofacial, head and neck surgery as artificial bone materials and as implants.

The random fiber-reinforced composites and the cured application oriented composites according to the invention have several advantages. The random oriented fiber bundles of the prepreg yield a toughening effect to the final cured product. Thus, for example the obtained cured dental materials are less prone to fractures and they follow more accurately the dental cavity. The fibers will decrease polymerization shrinkage resulting less marginal leakage between tooth and restoration.

From prior art it is known that restorative composites comprising micro-fibers suffer from extensive wear and they have weak mechanical properties, which can be partly explained based on the used fiber length being well below the critical fiber length. Critical fiber length means here the minimum fiber length where optimum stress transfer matrix to fiber occurs. In order to have the fibers to act as effective reinforcement for polymers, stress transfer from the polymer matrix to the fibers is essential. This is achieved, if the fibers have a length equal or greater than the critical fiber length. In the present invention the fiber length in the composite typically varies between 3 and 20 mm.

The longer fiber length improves also the handling properties as the fibers keep the composite together, and provides increased tapping pressure along the tooth cavity.

Further, the longer fiber length improves the alignment of fibers along the surface. The alignment of the fibers along the surface can also be improved by the applying thin layers having a layer thickness of under 0.5 mm, of the composite in a cavity or at a location of any other application. When the fibers are oriented at an angle not exceeding 30° and preferably approximately horizontally, significantly stronger structure is achieved according to Krenchel's principle.

From prior art it is known that short fibers, random in 3D orientation, provide a strengthening factor of 0.18, whereas fibers in 2D orientation give a factor of 0.38 and further fibers in unidirectional 1D orientation give a factor of 1. The orientation of the fibers in the composite according to the present invention, when applied and cured, reduces also thermal expansion, swelling caused by water absorption and polymerization shrinkage along the fibers of the restorative material.

The results of the mechanical tests presented in the examples revealed substantial improvements in load bearing capacity and flexural strength of dental composite resin reinforced with random E-glass fiber fillers in comparison with conventional restorative composites. Also composites manufactured from prepreg comprising highly viscous fiber bundles yielded clearly improved mechanical properties when compared with composites manufactured from fiber bundles pre-impregnated with low viscosity resin, as can be seen in FIG. 1, examples a) and b).

The flexural test has been widely used to characterize the mechanical properties of dental restorative materials. The composites according to the invention had a flexural strength of 211 MPa in 3-point bending test, whereas composite made from fiber bundles pre-impregnated with low viscosity resin had a flexural strength of only 140 Mpa, as can be seen in FIG. 1.

Figure 5:
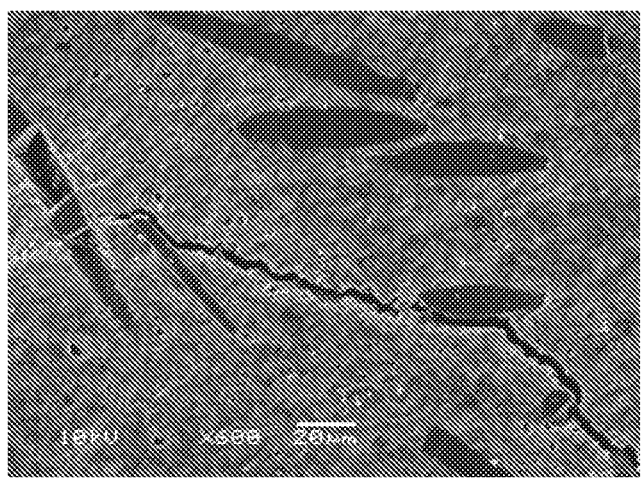
FIGS. 5A-5D are SEM photographs of polished surfaces of FC composite with a propagating crack.
Figure 5:
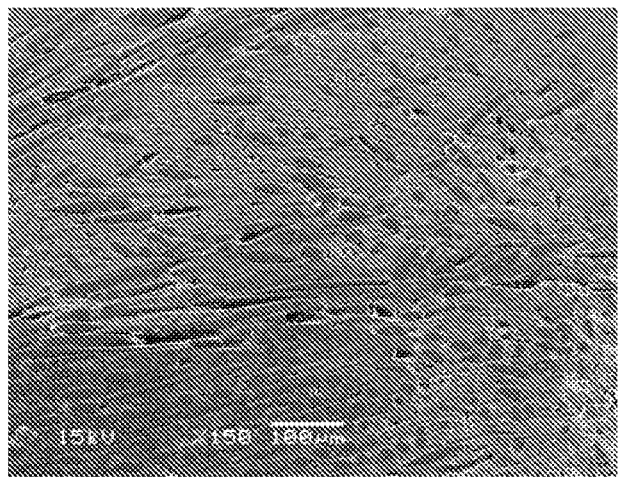
Figure 5:
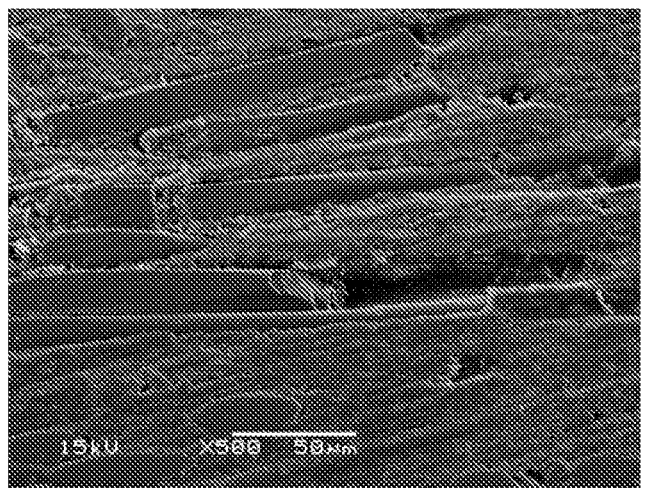
Figure 5:
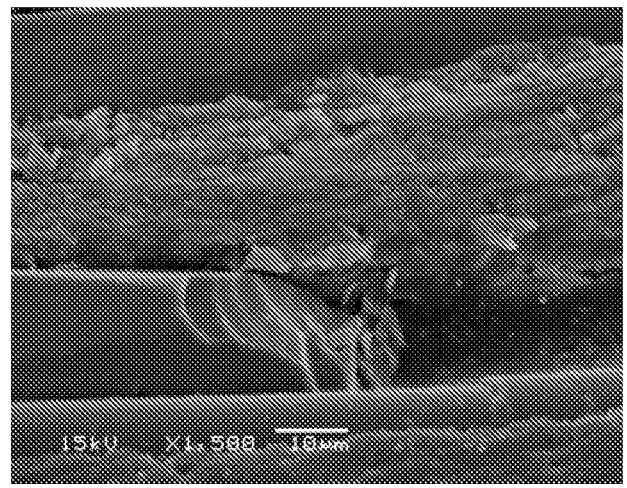

In addition, two times higher load-bearing capacity of the composite according to the invention was obtained compared to that of conventional particulate filler restorative composites. The reinforcing effect of fiber fillers is mainly based on stress transfer from polymer matrix to fibers, but also the behavior of individual fibers as a crack stopper has effect, as can be seen in FIG. 5.

FTIR was used for monitoring the propagation of polymerization at the bottom of the test material. The composite according to the invention showed slightly higher degree of conversion, which could be due to lower filler content in comparison with conventional composite Z250. However, some of the difference could be also explained by differences between polymer matrices of pure thermoset and semi-IPN matrices.

The manufacturing method provides a further advantage because the fibers are not agglomerated, because they are surrounded by the viscous protective polymer matrix of the prepreg. The fibers are more resistant to breakage during mixing and they are not cut to too small pieces, which would lead to loosing the strengthening effect. Because the fibers are pre-impregnated and protected by a matrix, desired wetting of fiber are ensured also with the matrix resin of the composite.

Further, the optimal orientation and anisotropy of the fibers result in a significant increase in the Krenchel's reinforcing factor, from 0.2 to 0.38 and even close tot in a packable/compactable product, wherein tapping or packing enforces the fibers in the desired orientation.

The composite according to the invention and particularly the fiber-reinforced semi-IPN composite exhibits clear improvements in mechanical properties compared with the conventional particulate filler restorative composite, resulting in better performance of glass fiber-reinforced composites in high stress-bearing application areas.

Further, the composite has reduced polymerization shrinkage in direct filling composite restorations, resulting in less leakage between the filling and cavity walls of teeth.

The invention is illustrated in the following with examples disclosing some preferable embodiments, to which however the invention is not limited.

EXAMPLES

Materials

The resin materials used in the examples are listed in following Table 1.

TABLE 1

Resin materials used in the examples

| Material | Manufacturer | Composition |
|---|---|---|
| Z250 (comparison) Conventional participate filler dental composite | 3M ESPE, USA | Bis-GMA, UDMA, Bis-EMA |
| EverStick | StickTeck Ltd, Finland | PMMA, Bis-GMA |
| Stick Resin | StickTeck Ltd, Finland | 60% Bis-GMA- 40% TEGDMA |

PMMA = polymethyl methacrylate, Mw 220.000
Bis-GMA = bisphenol A-glycidyl dimethacrylate.
TEGDMA = triethylenglycol dimethacrylate.
UDMA = urethane dimethacrylate
Bis-EMA = bisphenol A polyethylene glycol diether

Example 1

Manufacture of Random Fiber-Reinforced Composite a) Random fiber reinforced composite (FC) according to the invention was prepared by mixing 22.5 wt % of viscous resin (BisGMA-PMMA) embedded E-glass fibers (fiber prepreg, chopped to pieces (viscous bundles) having length of 10 mm) to 22.5 wt % of dimethacrylate-PMMA resin matrix and then 55 wt % of silanized filler particles of $SiO_2$ (3±2 μm in size) were added gradually. Polymerization initiator camphorquinone and activator DMAEMA was added to the mixture. The mixing was carried out using a high-speed mixer for 5 minutes (SpeedMixer, DAC). $SiO_2$ filler particles were silane-treated with MPS using conventional technique. In light initiated polymerization, the resin matrix of dimethacrylate-PMMA formed semi-IPN polymer matrix for the composite FC.

b) As a comparison (not belonging to the scope of the invention) the same weight % percentage of pure E-glass fiber were added to dimethacrylate-PMMA resin matrix as above and then 55 wt % of silanized filler particles of $SiO_2$ (3±2 μm in size) were added gradually and mixed in a similar manner. A comparative fiber composite without semi-IPN was obtained. This example also clearly shows that a significantly stronger fiber reinforced composites are obtained with the process according to the present invention, when compared with conventional manufacturing methods.

Example 2

Flexural Strength, Flexural Modulus, Flexural Toughness and Load Bearing Capacity Random fiber reinforced composites (FC) manufactured in Example 1a) and 1b) were tested according to ISO 4049 standard for mechanical properties. 3-point bending test specimens (2×2×25 mm$^3$) and compressive load bearing test specimens (9.5×5.5×3 mm$^3$) were made from experimental fiber composite FC and conventional particulate filler dental composite as comparative sample (Z250, 3M-ESPE). Bar-shaped specimens were made in a half-split stainless steel mold between transparent Mylar sheets and cubic specimens in open silicon mold covered by Mylar. Cubic specimens were fabricated by incrementally placing the materials in a silicon mold. In order to simulate the clinical condition, one additional test group was made by placing a bottom layer of FC (2.0 mm) as substructure and then conventional composite (1.0 mm) was applied subsequently after light initiated polymerization of the FC. Polymerization of the composite was made using a hand light-curing unit (Optilux-501, Kerr) for 40 s from both sides of the metal mold and incrementally from the top of silicon mold. The wavelength of the light was between 380 and 520 nm with maximal intensity at 470 nm and light intensity was 800 mW/cm$^2$. The specimens from each group (n=6) were either stored dry or water stored (37° C. for 30 days). The dry-stored (room temperature) specimens were tested 24 h after their preparation. Three-point bending test was conducted according to the ISO 4049 (test span: 20 mm, cross-head speed: 1.0 mm/min, indenter: 2 mm diameter). All specimens were loaded in material testing machine (model LRX, Lloyd Instrument Ltd) and the load-deflection curves were recorded with PC-computer software (Nexygen 4.0, Lloyd Instruments Ltd). Static compressive fracture test was carried to determine the load-bearing capacity of each group using a universal testing machine. Specimens were loaded using a steel ball (Ø3.0 mm) under until fracture.

Flexural strength ($\sigma_f$) and flexural modulus ($E_f$) were calculated from the following formula, $$\sigma_f = 3F_m l/(2bh^2)$$

$$E_f = Sl^3/(4bh^3)$$

where $F_m$ is the applied load (N) at the highest point of load-deflection curve, l is the span length (20.0 mm), b is the width of test specimens and h is the thickness of test specimens. S is the stiffness (N/m) S=F/d and d is the deflection corresponding to load F at a point in the straight-line portion of the trace. Toughness was calculated as the integral of the area under the stress/strain curve and reported in units of MPa.

The mechanical properties of random FC composite, manufactured in example 1a), 1b) and of commercial composite are presented in the following Table 2 and FIG. 1.

TABLE 2

| Mechanical properties of FC and commercial composite | | | | |
|---|---|---|---|---|
| Composite | Flexural Strength MPa | Flexural Modulus GPa | Flexural Toughness GPa | Load Bearing Capacity N |
| FC of example 1 a) | 210 | 13.5 | 0.23 | 1881 |
| Z250, commercial | 111 | 10.5 | 0.07 | 1031 |

Figure 2A:
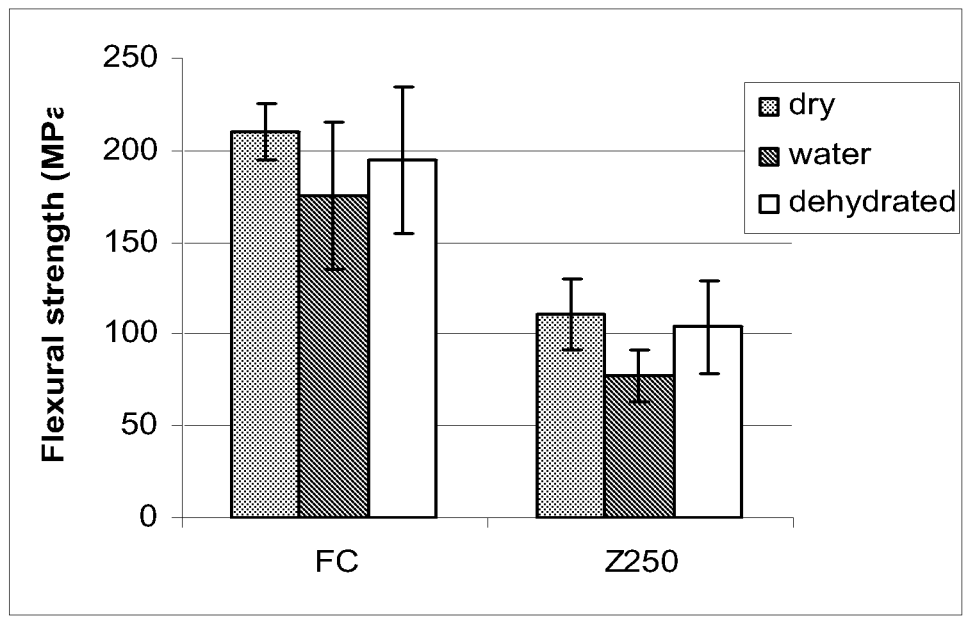
FIG. 2a presents a comparison of the flexural strength of FC composite and composite Z250.
Figure 2B:
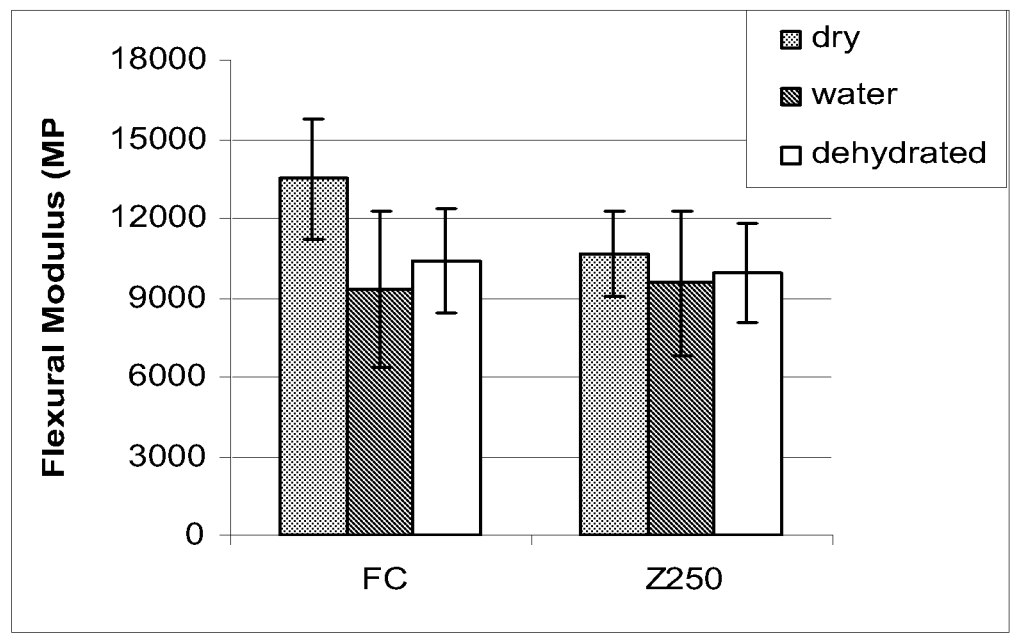
FIG. 2b presents a comparison of the flexural modulus of FC composite and composite Z250.
Figure 2C:
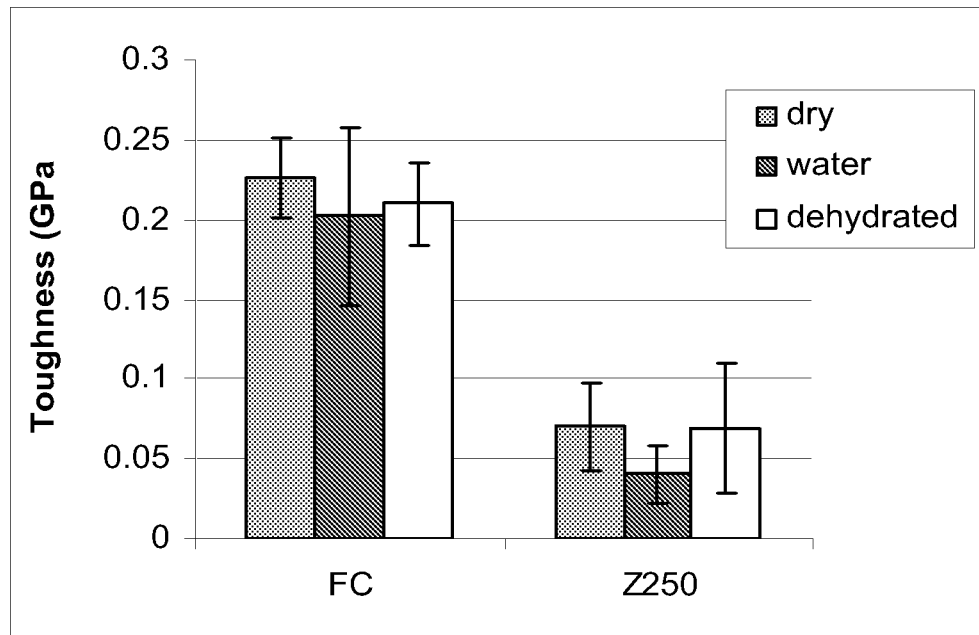
FIG. 2c presents a comparison of the flexural toughness of FC composite and composite Z250.

The mean flexural strength, flexural modulus and toughness, together with load-bearing capacity and degree of conversion of tested groups with standard deviations (SD) are summarized at FIGS. 2a-2c. ANOVA revealed that the FC composite had statistically significantly higher flexural strength of (210 MPa) and compressive load-bearing capacity of (1881 N) compared to comparative Z250 composite (111 MPa, N) (p<0.001) at dry conditions. Water storage decreased the flexural strength and the load-bearing capacity in both materials and with both tests (p<0.001) by an average of 20%.

In FIG. 1 a comparison of mechanical properties, particularly the flexural strength of conventional particle filler composite (Z250) and fiber reinforced composites with various fiber lengths and manufacturing technique is presented. FC 1a) is manufactured with high viscous fiber bindles whereas FC 1b) low viscous fiber bundles. Alert refers to commercial fiber-reinforced dental composite (Pentron Inc., USA) having microscale size (80-200 μm) size of fiber.

In FIG. 2a the flexural strength of FC (Ex. 1a) composite and commercial conventional restorative composite Z250 is presented. Groups: dry stored, water stored and water stored dehydrated. Vertical lines represent standard deviations. (Dry=after polymerization and conditioning, water=after water saturation for 30 days at 37° C., dehydrated=dehydration at 60° C.).

In FIG. 2b the flexural modulus of FC (Ex. 1a) composite and conventional restorative composite Z250 is presented. Vertical lines represent standard deviations. Groups: dry stored, water stored and water stored dehydrated.

In FIG. 2c flexural toughness of FC composite and conventional restorative composite Z250 is presented. Vertical lines represent standard deviations. Groups: dry stored, water stored and water stored dehydrated.

Figure 3:
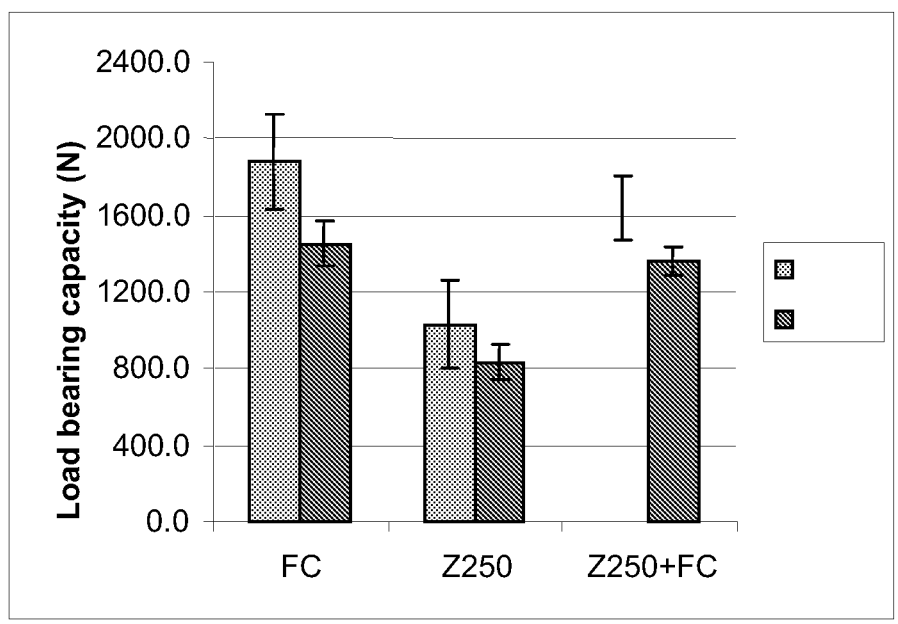
FIG. 3 presents compressive load bearing data.

In FIG. 3 compressive load bearing capacity of FC, a commercial control Z250 and a combination of commercial composite with FC is presented. Z250+FC refers to a specimen that was combined with a bottom layer (2.0 mm) of FC and covered with a 1.0 mm layer of Z250. Vertical lines represent standard deviations. Groups: dry stored and water stored.

Figure 4:
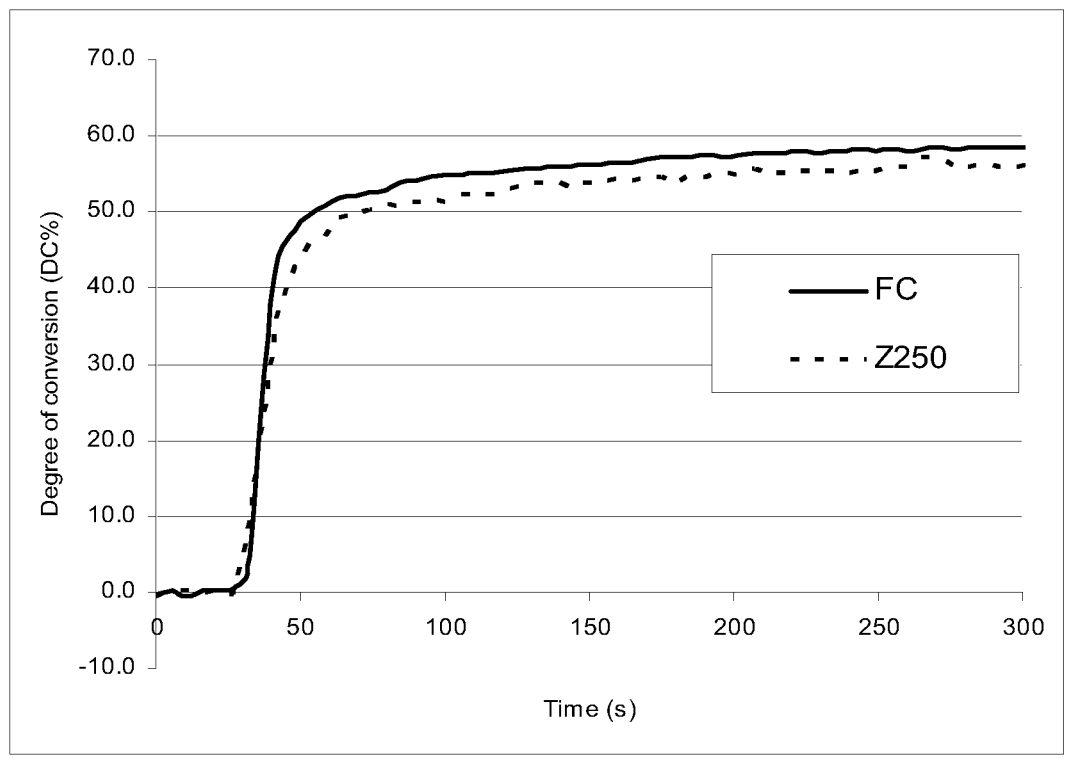
FIG. 4 presents degree of conversion data.

In FIG. 4 compressive load bearing capacity of FC, a commercial control Z250 and a combination of commercial composite with FC is presented. Z250+FC refers to a specimen that was combined with a bottom layer (2.0 mm) of FC and covered with a 1.0 mm layer of Z250. Vertical lines represent standard deviations. Groups: dry stored and water stored.

Example 3

Degree of Monomer Conversion

The degree of monomer conversion (DC %) of composite FC and comparative Z250 during and after photo-initiated polymerization was monitored by Fourier transformation infrared spectroscopy (FT-IR) with an attenuated total reflectance (ATR) sampling accessory. FTIR has proved to be a useful technique for the analysis of degree of monomer conversion in dental composites. The setup used was designed to simulate the conditions during the fabrication of direct restorations. The upper surface of the test material was exposed to the light source and the lower surface was in contact with the ATR crystal. Therefore, the experimental design here provides information about how the polymerization propagates on the bottom of the test material. The materials were placed in 1.8 mm-thick ring molds with a diameter of 6.5 mm on the ATR-sensor (ZnSe-crystal). The upper surface of the specimen was covered with a Mylar sheet and a glass slide of 1 mm thickness and slightly pressed against the ATR to ensure the good contact of the specimen. The light source was placed in contact with glass surface. The substrate was light-polymerized with a hand-held light curing unit (Freelight 2, 3M ESPE) for 40 s. The spectra during the polymerization process was recorded every 6 s until 5 min. The DC % was calculated from the aliphatic C=C peak at 1638 cm$^{-1}$ and normalized against the aromatic C=C peak at 1608 cm$^{-1}$ according to the following formula:

$$DC\% \left[1 - \frac{C_{aliphatic} / C_{aromatic}}{U_{aliphatic} / U_{aromatic}}\right] 100\%$$

where:
$C_{aliphatic}$=absorption peak at 1638 cm$^{-1}$ of the cured specimen
$C_{aromtic}$=absorption peak at 1608 cm$^{-1}$ of the cured specimen
$U_{aliphatic}$=absorption peak at 1638 cm$^{-1}$ of the uncured specimen
$U_{aromatic}$=absorption peak at 1608 cm$^{-1}$ of the uncured specimen The fraction of remaining double bonds for each spectrum was determined by standard baseline techniques using the comparison of maximum heights of aliphatic and reference peaks for calculations.

Degree of monomer conversion after 5 min of light-polymerization of FC composite manufactured in example 1a) was 58% (1.8) and Z250 composite 55% (1.2). In FIG. 4 the degree of monomer conversion (DC %) of composite FC and composite Z250 light-polymerized with light curing unit for 40 s is presented.

Example 4

Scanning Electron Microscopy

Scanning electron microscopy (SEM, Jeol Ltd) was used to evaluate the structure of polymer matrix, orientation of fibers and fracture surface of FC composite. Cross-sections of test specimens were wet ground using silicon carbide grinding paper by a grinding machine LaboPol-21 (Struers A/S). Mean values of flexural properties, load-bearing capacity, degree of monomer conversion and water sorption were statistically analyzed with analysis of variance (ANOVA) at the P<0.05 significance level to determine the differences between the groups.

SEM-micrographs of surface revealed microstructure of combination of fibers and particulate fillers. Fibers acted as crack stoppers and provided increase in fracture resistance and fracture stopping. In FIGS. 5A-5D SEM photographs of polished surface of FC composite with a propagating crack (A) is presented. Fracture surface with different magnifications showing fractured glass fiber is presented in (B), (C) and (D).

Example 5

Polymerization Shrinkage

The Random FC manufactured in Example 1a) and a commercial composite were tested for shrinkage upon polymerization. Two different methods were applied in order to observe the effect of application orientation for Random FC. Volumetric shrinkage was measured with a LAUDA C6 CP volume dilatometer. The volume dilatometer determines the reduction of volume according to Archimedes' law.

The dilatometer glass capillary was filled with a non-polymerized sample. An exactly weighted sample size was 0.3-0.5 grams. Samples were degassed and the rest of the capillary was filled with mercury. Volume data collection was started and the sample was cured with the hand-curing unit (Optilux-501, Kerr) through glass wall of the capillary for 60 seconds to start the polymerization reaction. The recording of volumetric change was finished after 48 hours from the polymerization. Just prior to end of the period, the possible voids in the samples were removed by dipping the capillaries in liquid nitrogen, allowing the samples to warm-up to ambient temperature again and the recording was stopped. The volumetric polymerization shrinkage values for the Random FC composite manufactured in Example 1a) and for some commercial composites are listed in Table 3 below. Shrinkage after application orientation is measured using strain gage technique, where composite is applied as a thin 1.0 mm layer on the strain gage. Table 3 reveals that FC has clearly higher volumetric shrinkage, whereas shrinkage of FC composite after application orientation technique results to same level to commercial particle composite Z250.

TABLE 3

Shrinkage values of FC and commercial dental composite

| | Volumetric Shrinkage (% vol) | Shrinkage Strain (μ-strain) |
|---|---|---|
| FC | 3.05% (±0.25%) | 0.67% (±0.15%) |
| Z250 | 1.80% (±0.25%) | 0.65 (±0.03%) |

From the shrinkage strain values it is observed that random FC after application orientation technique has same shrinkage than conventional particle filled composite.

Example 6

Preparation of Bioactive Fiber Composite

Flexural strength of FC was measured after adding either 20% or 40% weight % of bioactive glass particle (BAG)

Figure 6:
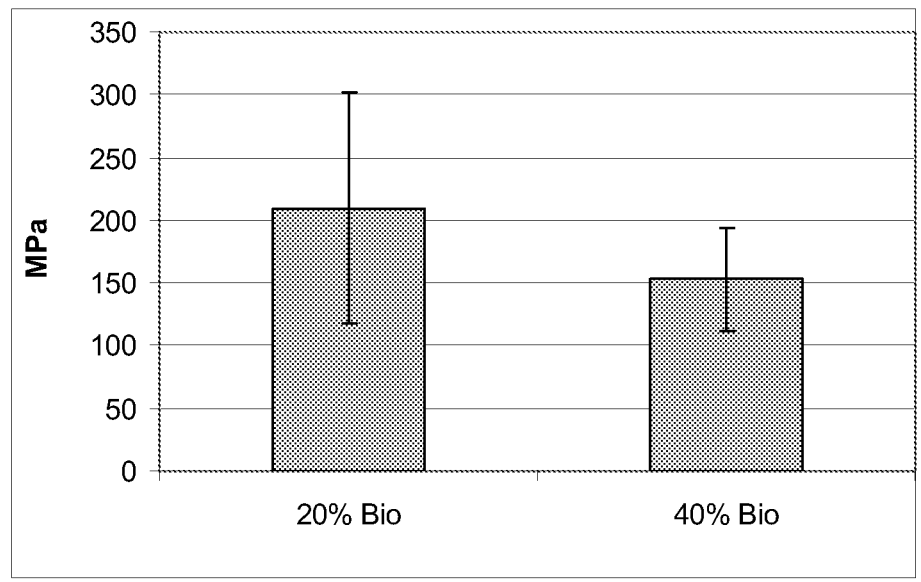
FIG. 6 illustrates the flexural strength of FC after adding bioactive glass particles.

(Vivoxid, Turku) to FC. By adding BAG particles high mechanical properties were obtained. Bioactive FC can be used in dental application (eg. to treat hypersensitive teeth) and medical application such as bone cement or bone support device in maxillofacial reconstruction or support plates. In FIG. 6 the flexural strength of FC after adding either 20 wt % or 40 wt % of bioactive glass particles is illustrated.

When the application is bone cement, auto-polymerization initiator/activator system is suitably used by adding the initiator and activator to separate composites, which are mixed together just prior the operation.

Example 7

Dual Cured Fiber Composite

Dual cured cement of FC is prepared using both light initiator (camphorquinone)/activator (DMAEMA) system and auto-polymerization system together. Dual cured system is needed especially when FC is used to cement dental prostheses or root canal post. Also temporary crown and bridge composite is typically used as a dual cured system.

Example 8

Application of FC Using Syringe

When FC is applied using syringe, FC is highly oriented reaching Krenchel's factor of close to 1. In this form FC can be used eg. when splinting teeth together or inserting FC into root canal forming in situ polymerized root canal post.

The invention claimed is:
1. A curable fiber-reinforced composite for direct restoration, said composite comprising:
(a) 10-60 wt-% of a monomer system comprising at least one curable monomer selected from dimethacrylates, acrylates, methacylates, epoxides, dimethacrylates of polyethyleneglycols, and light curable biodegradable resins;
(b) 40-90 wt-% of a filler system comprising (i) at least one prepreg comprising highly viscous bundles of fibers, selected from the group consisting of fibers of bioactive glass, glass fibers, alumina fibers, zirconia fibers, metallic fibers, ceramic fibers, carbon/graphite fibers, polymeric fibers, self-reinforced polymer fibers, fibers based on polyphenols, degradable and biodegradable fibers, sol-gel derived silica fibers, and mixtures thereof, said fibers having fiber diameters of 0.05-100 μm and fiber lengths of 0.5-100 mm in a polymer matrix having a viscosity of at least 500 Pa·s, wherein the prepreg is in the form of pieces having a length of 3-20 mm, (ii) 0-80 wt-% of at least one particulate filler selected from conventional particulate fillers having a particle size of 0.1-100 μm and nanoscale particulate fillers having a particle size of less than 0.1 μm, and (iii) polymeric matrix; and
(c) a polymerization initiator(s) and/or a polymerization accelerator(s),
wherein said components (a), (b), and (c) are compounded together, thereby forming an application-orientated curable material which provides reduced polymerization shrinkage in direct composite restorations.

2. The curable fiber-reinforced composite according to claim 1, characterized in that it comprises (a) 15-30 wt-% of the monomer system and (b) 70-85 wt-% of the filler system.

3. The curable fiber-reinforced composite according to claim 1, characterized in that the curable monomers of the monomer system are selected from bisphenol A-glycidyl dimethacrylate, bisphenol A polyethyleneglycol diether, triethyleneglycol dimethacrylate, tetraethyleneglycol dimethacrylate, neopentylglycol dimethacrylate, hydroxyethyl methacrylate, methyl methacrylate and acrylate, urethane dimethacrylate, 1,3- and 1,4-butanediol dimethacrylate, 1,6-hexanediol dimethacrylate, methylmethacrylate and 2-hydroxyethanol methacrylate.

4. The curable fiber-reinforced composite according to claim 1, characterized in that the conventional particulate filler is selected from color pigments, inert ceramics, xerogels, inorganic salts, bioactive or bio-soluble glasses and combinations thereof and the nanoscale particulate fillers are selected from inorganic fillers, organic polymer fillers and organic-inorganic silsesquioxane based fillers.

5. The curable fiber-reinforced composite according to claim 1, characterized in that the conventional particulate filler is selected from phosphates and oxides of Si, Ba, AL, Ca, P, Ba, Zr, Al, Mg, K, Na, and Ti.

6. A dental or medical composition comprising the curable fiber-reinforced composite according to claim 1.

7. The dental or medical composition use according to claim 6, wherein the dental composition is a component of a restorative prosthodontic material, a core composite, an adhesive, a liner, a cementing and luting material, a cavity filling material, a root canal post-cementing material, a provisional and semi-permanent crown and bridge composite material or a CAD/CAM block, and the medical composition is a component of an orthopedic bone cement, a bone support device for maxillofacial, head and neck surgery or an implant.

8. The curable fiber-reinforced composite according to claim 1, characterized in that the conventional particulate filler is selected from fumed silica, colloidal silica, amorphous silica, quartz, alumina silicate, barium silicate glass, fluorosilicate glass, zirconia, calcium oxides, hydroxyapatites, titania, and calcium phosphate.

9. The curable fiber-reinforced composite according to claim 1, characterized in that the fibers are selected from fibers having a diameter of 1-25 μm.

* * * * *